US00PP24801P2

(12) United States Plant Patent
de Bont

(10) Patent No.: US PP24,801 P2
(45) Date of Patent: Aug. 19, 2014

(54) ***ECHINACEA* PLANT NAMED 'EGLOW'**

(50) Latin Name: ***Echinacea* hybrid**
Varietal Denomination: Eglow

(71) Applicant: Dionysius F. M. de Bont, Gouda (NL)

(72) Inventor: Dionysius F. M. de Bont, Gouda (NL)

( * ) Notice: Subject to any disclaimer, the term of this patent is extended or adjusted under 35 U.S.C. 154(b) by 0 days.

(21) Appl. No.: 13/986,117

(22) Filed: Apr. 3, 2013

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of hybrid *Echinacea*, 'Eglow', characterized by its inflorescences with red cones and ray florets that are held horizontally and open light yellow with a darker orange-yellow base and mature to orange-yellow with a red base, and by its strong and erect stems.

2 Drawing Sheets

Botanical classification: *Echinacea* hybrid.
Variety denomination: 'Eglow'.

BACKGROUND OF THE INVENTION

The present invention relates to a new and distinct cultivar of *Echinacea* of hybrid origin and will be referred to hereafter by its cultivar name, 'Eglow'. 'Eglow' represents a new coneflower, an herbaceous perennial grown for landscape use.

The Inventor selected the new cultivar, 'Eglow', in a seedbed at a nursery in Sint Annaland, The Netherlands in August of 2008. The seedbed had been planted with seeds collected and pooled from unnamed proprietary plants of *Echinacea purpurea* and unnamed proprietary plants of hybrid *Echinacea*. The exact parents are therefore unknown.

Asexual propagation of the new cultivar was first accomplished by in vitro propagation under the direction of the Inventor in Rijswijk, The Netherlands in September of 2010. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Eglow' as a unique cultivar of *Echinacea*.

1. 'Eglow' exhibits inflorescences with red cones and ray florets that are uniquely colored; opening light yellow with the base darker orange-yellow and maturing to orange-yellow with a red base.
2. 'Eglow' exhibits ray florets that are held horizontal.
3. 'Eglow' exhibits strong stems that are held erect.

The new cultivar can be most closely compared to the cultivars 'Flame Thrower' (U.S. Plant Pat. No. 21,932) and 'Tiki Torch' (U.S. Plant Pat. No. 18,839). 'Flame Thrower' is similar to 'Eglow' in ray floret color, however 'Flame Thrower' differs from 'Eglow' in having ray florets that are held slightly less flat and lack pink coloration at the base, and in being taller in height. 'Tiki Torch' is similar to 'Eglow' in having orange ray florets, however 'Tiki Torch' differs from 'Eglow' in having larger inflorescences with ray florets that are deeper orange without pink coloration and drooping in aspect, and in having a taller plant height.

BRIEF DESCRIPTION OF THE DRAWINGS

The plants in the accompanying photographs depict the characteristics of a six month-old plant of 'Eglow' as field grown in Sint Annaland, The Netherlands and placed in a one-gallon container for the photographs.

The photograph in FIG. 1 provides a side view of a plant in bloom.

Figure 1:
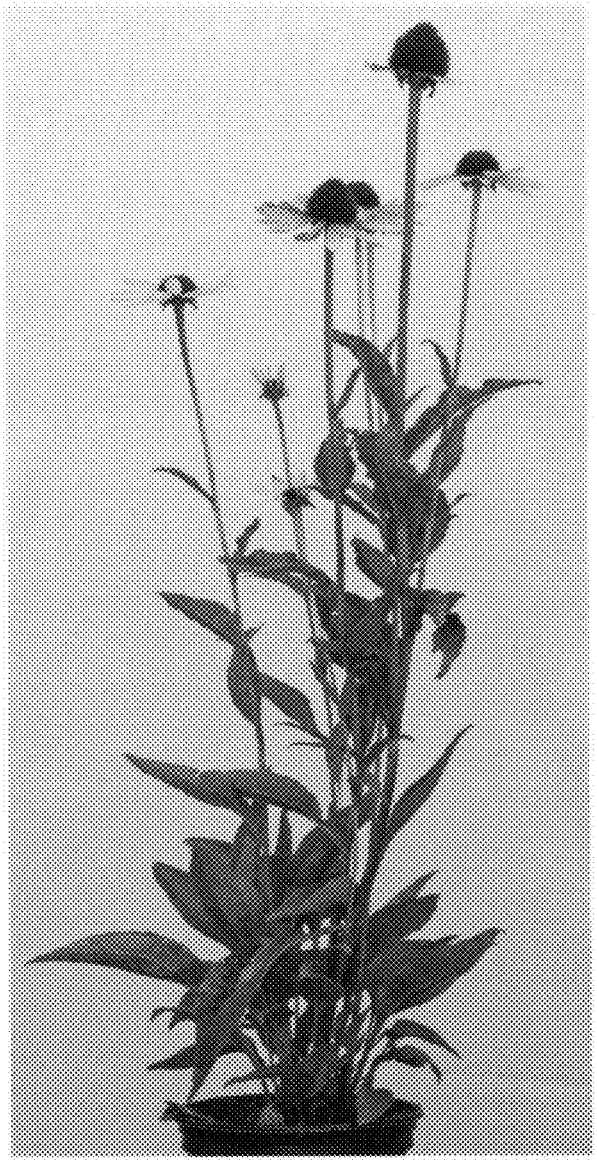
Figure 2:
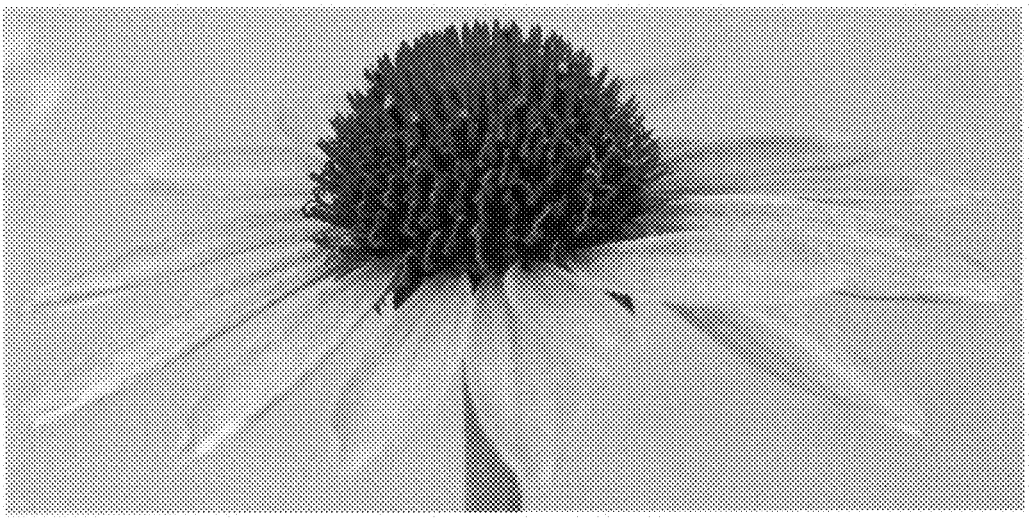

The photograph in FIG. 2 provides a close-up view of an inflorescence of 'Eglow'.

Figure 3:
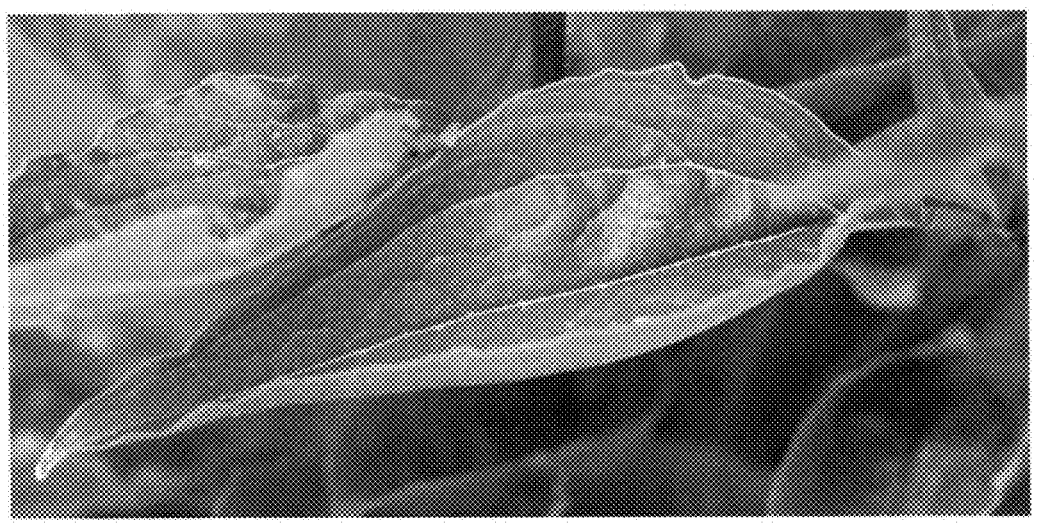

The photograph in FIG. 3 provides a close-up view of a leaf of 'Eglow'.

The colors in the photograph may differ slightly from the color values cited in the detailed botanical description, which accurately describe the colors of the new *Echinacea*.

BOTANICAL DESCRIPTION OF THE PLANT

The following is a detailed description of six month-old plants of 'Eglow' as field grown in Sint Annaland, The Netherlands. Plants were grown under average day temperatures ranging from 15° to 32° C. and average night temperatures of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July into September in The Netherlands.

*Plant type*.—Herbaceous perennial.

*Plant habit*.—Clump forming, upright with strong and erect flowering stems.

*Height and spread*.—About 75 cm in height and 40 cm in spread.

*Cold hardiness*.—At least to U.S.D.A. Zones 3.

*Diseases and pests*.—Not particular susceptible or resistance to pests or diseases has been observed.

*Root description*.—Fibrous.

Growth and propagation:

*Propagation*.—Tissue culture.

*Growth rate*.—Moderate to highly vigorous.

Stem description:

*Shape*.—Rounded.

*Stem color*.—144A to 144B, slightly tinged on the sunny side ranging between 165A and 177A.

*Stem size*.—Average of 4 mm in diameter and an average of 48.1 cm in height.

*Stem surface*.—Slightly rough to the touch due to being covered with sparse strigose pubescence; 1 mm in length, NN155D in color.

*Stem strength*.—Strong.

*Stem number*.—Average of 5 main stems.

*Branching*.—Un-branched.

*Stem aspect*.—Held erect.

Foliage description:

*Leaf shape*.—Ovate to narrowly ovate.

*Leaf division*.—Simple.

*Leaf base*.—Attenuate.

*Leaf apex*.—Long acute.

*Leaf venation*.—Pinnate, upper surface color; 145B, lower surface color; 145A to 145B.

*Leaf margins*.—Entire to coarsely and shallowly dentate, wavy.

*Leaf attachment*.—Petiolate.

*Leaf arrangement*.—Alternate.

*Internode length*.—An average of 4.9 cm.

*Leaf size*.—Average of 11.7 cm in length and 5.4 cm in width.

*Leaf color*.—Young upper surface; 134A, young lower surface; 143A to 143B, mature upper surface; N137A to N137B, mature lower surface; 137B.

*Leaf surface*.—Upper surface is very slightly glossy, lower surface is slightly glossy, both surfaces moderately covered with very short strigose hairs; average length of 0.5 mm and 155D in color.

*Petioles*.—Upper stem leaves nearly sessile, average length of petioled leaves is 5.4 cm in length, v-shaped petiole is about 4 mm in length and width, color; upper side 145A, margins N137B, lower side 145B, margin 137A, main vein sparsely covered with very short strigose hairs, average of 0.3 mm in length and 155D in color.

Flower description:

*Type*.—Terminal capitulum, heterogamous with ray florets around the head margin and disk florets in the center, forming a radiant head.

*Capitulum number*.—One terminal capitulum per stem.

*Lastingness of inflorescence*.—About 10 days.

*Capitulum size*.—Matures to about 2.9 cm in height and 9.4 cm in diameter, disk size is an average of 3 cm in diameter.

*Fragrance*.—Faint, sweet but slightly acidic fragrance.

*Involucral bracts or phyllary*.—About 50 arranged in 3 overlapping rows, up to 8 mm in length and 3 mm in width, dull in appearance, cuneate at base, acute apex, ovate to narrow ovate in shape, entire margins moderately covered with very short hairs; 0.5 mm in length and 155D in color, upper surface; smooth and N143C, base 145D in color, lower surface; 137C in color and sparsely covered with very short hairs average of 0.5 mm in length and 155D in color.

*Buds*.—Flattened globular in shape, up to 2.7 cm in diameter and 2.5 cm in length, color; 143A, immature ray florets 11C, immature receptacle spines 183A.

*Peduncle*.—Strong, straight on top of main (flowering) stem, average angle of secondary and tertiary peduncles 20° (0°=straight upright), terminal peduncle length is 11.3 and 3 mm in diameter, 144C, becoming 144B near the inflorescence, surface is covered with short strigose hairs, 1 mm in length and NN155D in color.

*Ray florets*.—Rotate, about 17, oblanceolate in shape, about 4.4 cm in length and 1.1 cm in width, praemorse apex, cuneate base, entire margin, slightly drooping in an average of 5° downward near horizontal, upper surface texture is smooth, moderately velvety and moderately ribbed lengthways (carinate), lower surface texture is smooth and moderately ribbed lengthways (carinate), color: when opening upper surface; 13A, base becoming 22B, when opening lower surface; 12D, when fully open upper surface; 22A, base 53D, when fully open lower surface; 58D, center 150D, upper surface fading to 53D, upper half tinged 22B, tip tinged 1B, lower surface fading to 59D, striped with 150D, tip 144C.

*Disk florets* (*bisexual*).—Numerous, about 240, tubular in shape, fused into tube upper 10% free, acute apex, base fused into tube, about 1 cm in length and 2 mm in width, entire margin, upper and lower surfaces smooth and glossy in appearance, color of upper and lower surfaces when opening; 146B, outer tip 183B to 183C, mid-section 145C, base 150D, color of upper and lower surfaces with fully open; 187A, upper half of mid-section 187C to 187D, lower half of mid-section 144C, base 150D.

*Receptacle*.—Triangular in shape, about 0.9 cm in diameter and height, color 157D.

*Receptacle spines*.—Average of 240, average of 1.3 cm in length, acicular in shape, acute apex, attenuate base, smooth and glossy surface, color: apex; 45A to 46A, mid-section; 144C, base; 145D.

Reproductive organs (present on disk florets only):

*Gynoecium*.—Pistil; 1,1 cm in length, style; 9 mm in length and 145A in color, ovary; 150D in color.

*Androcoecium*.—Stamens; 4, filament 3 mm in length and 150D in color, anther; linear in shape, 3 mm in length and 200A in color, pollen; moderate in quantity and 15A in color.

*Fruit/seed*.—No fruit or seed detected to date.

It is claimed:

1. A new and distinct cultivar of *Echinacea* plant named 'Eglow' substantially as herein illustrated and described.

* * * * *